United States Patent
Toender et al.

(10) Patent No.: US 8,822,188 B2
(45) Date of Patent: Sep. 2, 2014

(54) USE OF ENZYMES HAVING SILICASE ACTIVITY

(75) Inventors: Janne Ejrnæs Toender, Vaerloese (DK); Martin Borchert, Alleroed (DK)

(73) Assignee: Novozymes A/S, Bagsvaerd (DK)

( * ) Notice: Subject to any disclaimer, the term of this patent is extended or adjusted under 35 U.S.C. 154(b) by 50 days.

(21) Appl. No.: 13/132,850

(22) PCT Filed: Dec. 18, 2009

(86) PCT No.: PCT/EP2009/067551
§ 371 (c)(1),
(2), (4) Date: Jun. 3, 2011

(87) PCT Pub. No.: WO2010/070110
PCT Pub. Date: Jun. 24, 2010

(65) Prior Publication Data
US 2012/0021480 A1    Jan. 26, 2012

Related U.S. Application Data

(60) Provisional application No. 61/139,066, filed on Dec. 19, 2008.

(30) Foreign Application Priority Data

Dec. 19, 2008    (EP) .................................... 08172374

(51) Int. Cl.
*C12P 3/00*    (2006.01)
*C12P 9/00*    (2006.01)
*C12N 9/16*    (2006.01)
*C07H 21/04*    (2006.01)
*C07K 1/00*    (2006.01)

(52) U.S. Cl.
USPC .......... 435/168; 435/131; 435/196; 536/23.2; 530/350

(58) Field of Classification Search
USPC .......... 435/168, 131, 196; 536/23.52; 530/350
See application file for complete search history.

(56) References Cited

U.S. PATENT DOCUMENTS

| 7,229,807 B2 | 6/2007 | Muller et al. | |
| 8,119,387 B2 * | 2/2012 | Nielsen et al. | 435/232 |
| 2007/0218044 A1 | 9/2007 | Muller et al. | |
| 2008/0293096 A1 | 11/2008 | Muller et al. | |

OTHER PUBLICATIONS

Broun et al., Catalytic plasticity of fatty acid modification enzymes underlying chemical diversity of plant lipids. Science, 1998, vol. 282: 1315-1317.*
Devos et al., Practical limits of function prediction. Proteins: Structure, Function, and Genetics. 2000, vol. 41: 98-107.*
Seffernick et al., Melamine deaminase and Atrazine chlorohydrolase: 98 percent identical but functionally different. J. Bacteriol., 2001, vol. 183 (8): 2405-2410.*
Whisstock et al., Prediction of protein function from protein sequence. Q. Rev. Biophysics., 2003, vol. 36 (3): 307-340.*
Witkowski et al., Conversion of b-ketoacyl synthase to a Malonyl Decarboxylase by replacement of the active cysteine with glutamine. Biochemistry, 1999, vol. 38: 11643-11650.*
Alber et al., "A carbonic anhydrase from the archaeon *Methanosarcina thermophila*", Proc Natl Acad Sci USA, vol. 91, pp. 6909-6913 (1994).
Brandstadt, "Inspired by nature: an exploration of biocatalyzed siloxane bond formation and cleavage", Curr Op Biotechnol., vol. 16, pp. 393-397 (2005).
Cha et al., "Silicatein filaments and subunits from a marine sponge direct the polymerization of silica and silicones in vitro", Proc Natl Acad Sci USA, vol. 96, pp. 361-365 (1999).
Douglas et al., Crystal Structures of Silica and Metal Silicates, Structure Chemistry of Crystalline Solids, Springer, New York, Chap 10, pp. 233-278 (2006).
Schroeder et al., "Enzymatic production of biosilica glass using enzymes from sponges: basic aspects and application in nanobiotechnology (material sciences and medicine)," Naturwissenschaften, vol. 94, pp. 339-359 (2007).
Schroeder et al., "Silicase, an enzyme which degrades biogenous amorphous Silica: contribution to the metabolism of silica deposition in the demosponge *Suberites domuncula*", Progress Mol Subcellular Biol 33, 249-268 (2003).
Shimizu et al., "Silicatein α: Cathepsin L-like protein in sponge biosilica", Proc Natl Acad Sci USA, vol. 95, pp. 6234-6238 (1998).
Zhou et al., "Efficient Catalysis of Polysiloxane Synthesis by Silicatein a Requires Specific Hydroxy and Imidazole Functionalities", Angew Chem Int Ed., vol. 38, No. 6, pp. 780-782 (1999).

* cited by examiner

*Primary Examiner* — Ganapathirama Raghu
(74) *Attorney, Agent, or Firm* — Elias Lambiris

(57) ABSTRACT

The present disclosure relates to the use of polypeptides having silicase activity for the modification or synthesis of silica, silicones and other silicium (IV) compounds. The present invention also relates to the use of polypeptides having silicase activity for the modification of glass, sand, asbestos, computer chips, glass wool, fiber glass, optical fibers and silicones, for the removal of sand from oil-sands, for the removal of asbestos, and for sandblasting.

15 Claims, No Drawings

SEQUENCE LISTING

```
<160> NUMBER OF SEQ ID NOS: 12

<210> SEQ ID NO 1
<211> LENGTH: 247
<212> TYPE: PRT
<213> ORGANISM: Methanosarcina thermophila

<400> SEQUENCE: 1

Met Met Phe Asn Lys Gln Ile Phe Thr Ile Leu Ile Leu Ser Leu Ser
1               5                   10                  15

Leu Ala Leu Ala Gly Ser Gly Cys Ile Ser Glu Gly Ala Glu Asp Asn
            20                  25                  30

Val Ala Gln Glu Ile Thr Val Asp Glu Phe Ser Asn Ile Arg Glu Asn
        35                  40                  45

Pro Val Thr Pro Trp Asn Pro Glu Pro Ser Ala Pro Val Ile Asp Pro
    50                  55                  60

Thr Ala Tyr Ile Asp Pro Gln Ala Ser Val Ile Gly Glu Val Thr Ile
65                  70                  75                  80

Gly Ala Asn Val Met Val Ser Pro Met Ala Ser Ile Arg Ser Asp Glu
                85                  90                  95

Gly Met Pro Ile Phe Val Gly Asp Arg Ser Asn Val Gln Asp Gly Val
            100                 105                 110

Val Leu His Ala Leu Glu Thr Ile Asn Glu Glu Gly Glu Pro Ile Glu
        115                 120                 125

Asp Asn Ile Val Glu Val Asp Gly Lys Glu Tyr Ala Val Tyr Ile Gly
    130                 135                 140

Asn Asn Val Ser Leu Ala His Gln Ser Gln Val His Gly Pro Ala Ala
145                 150                 155                 160

Val Gly Asp Asp Thr Phe Ile Gly Met Gln Ala Phe Val Phe Lys Ser
                165                 170                 175

Lys Val Gly Asn Asn Cys Val Leu Glu Pro Arg Ser Ala Ala Ile Gly
            180                 185                 190

Val Thr Ile Pro Asp Gly Arg Tyr Ile Pro Ala Gly Met Val Val Thr
        195                 200                 205

Ser Gln Ala Glu Ala Asp Lys Leu Pro Glu Val Thr Asp Asp Tyr Ala
    210                 215                 220

Tyr Ser His Thr Asn Glu Ala Val Val Tyr Val Asn Val His Leu Ala
225                 230                 235                 240

Glu Gly Tyr Lys Glu Thr Ser
                245
```

<210> SEQ ID NO 2
<211> LENGTH: 236
<212> TYPE: PRT
<213> ORGANISM: Bacillus licheniformis

<400> SEQUENCE: 2

```
Met Lys Leu Ser Ser Lys Leu Ile Leu Gly Leu Thr Val Ser Ser Leu
1               5                   10                  15

Ala Gly Lys Phe Leu Glu Lys Leu Leu Ile Gln Asp Asn Val Ser Pro
            20                  25                  30

Asn Ile Thr Ala Ser Phe Asn Gln Glu Ala Asp Ile Pro Asp Ile Asp
        35                  40                  45

Ala Ser Ser Tyr Ile His His Phe Ala Ser Val Ile Gly Ser Val Val
    50                  55                  60

Ile Gly Arg Asn Val Phe Ile Gly Pro Phe Ser Ser Ile Arg Gly Asp
65                  70                  75                  80

Val Gly Leu Lys Ile Phe Ile Ser His Asp Cys Asn Ile Gln Asp Gly
                85                  90                  95

Val Val Leu His Gly Leu Lys Asn Tyr Glu Tyr Asn Ser Pro Val Thr
            100                 105                 110

Glu His Ser Val Phe Lys Asp Arg Glu Ser Tyr Ser Ile Tyr Ile Gly
        115                 120                 125

Glu Lys Val Ser Leu Ala Pro Gln Cys Gln Ile Tyr Gly Pro Val Arg
    130                 135                 140

Ile Asp Lys Asn Val Phe Val Gly Met Gln Ser Leu Val Phe Asp Ala
145                 150                 155                 160

Tyr Ile Gln Glu Asp Thr Val Ile Glu Pro Gly Ala Lys Ile Ile Gly
                165                 170                 175

Val Thr Ile Pro Pro Lys Arg Phe Val Ser Ala Gly Arg Val Ile Ser
            180                 185                 190

Asn Gln Glu Asp Ala Asn Arg Leu Pro Glu Ile Thr Asp Ser Tyr Pro
        195                 200                 205

Tyr His Asp Leu Asn Ser Lys Met Thr Ser Val Asn Leu Glu Leu Ala
    210                 215                 220

Lys Gly Tyr Lys Lys Glu Glu Arg Gln Trp Lys Leu
225                 230                 235
```

<210> SEQ ID NO 3
<211> LENGTH: 205
<212> TYPE: PRT
<213> ORGANISM: Pelobacter carbinolicus

<400> SEQUENCE: 3

```
Met Ile Glu Lys Asn Val Val Thr Asp Phe Cys Ser Glu Ala Ser Glu
1               5                   10                  15

Pro Val Ile Asp Ala Ser Thr Tyr Val His Pro Leu Ala Ala Val Ile
            20                  25                  30

Gly Asn Val Ile Leu Gly Lys Asn Ile Met Val Ser Pro Thr Ala Val
        35                  40                  45

Val Arg Gly Asp Glu Gly Gln Pro Leu His Val Gly Asp Ser Asn
    50                  55                  60

Ile Gln Asp Gly Val Val Ile His Ala Leu Glu Thr Glu Met Asn Gly
65                  70                  75                  80

Lys Pro Val Ala Lys Asn Leu Tyr Gln Val Asp Gly Arg Ser Tyr Gly
                85                  90                  95
```

```
Ala Tyr Val Gly Cys Arg Val Ser Leu Ala His Gln Val Gln Ile His
            100                 105                 110

Gly Pro Ala Val Val Leu Asp Asp Thr Phe Val Gly Met Lys Ser Leu
            115                 120                 125

Val Phe Lys Ser Phe Val Gly Lys Gly Cys Val Ile Glu Pro Gly Ser
        130                 135                 140

Ile Val Met Gly Val Thr Val Ala Asp Gly Arg Tyr Val Pro Ala Gly
145                 150                 155                 160

Ser Val Ile Arg Thr Gln Glu Asp Ala Asp Ala Leu Pro Glu Ile Gly
                165                 170                 175

Ala Asp Tyr Pro Phe Arg Ala Met Asn Pro Gly Val Val His Val Asn
            180                 185                 190

Thr Ala Leu Ala Lys Gly Tyr Met Val Lys Gln Gly Asn
            195                 200                 205

<210> SEQ ID NO 4
<211> LENGTH: 204
<212> TYPE: PRT
<213> ORGANISM: Syntrophus aciditrophicus

<400> SEQUENCE: 4

Met Ile Gly Lys Asn Val Leu Thr Asp Phe Ser Ala Arg Ala Ser Glu
1               5                   10                  15

Pro Val Ile Gly Ser Phe Thr Phe Val His Pro Leu Ala Ala Val Ile
            20                  25                  30

Gly Asn Val Ile Leu Gly Asp Asn Ile Met Val Ser Pro Gly Ala Ser
        35                  40                  45

Ile Arg Gly Asp Glu Gly Gln Pro Leu Tyr Val Gly Ser Asp Ser Asn
50                  55                  60

Val Gln Asp Gly Val Val Ile His Ala Leu Glu Thr Glu Leu Asp Gly
65                  70                  75                  80

Lys Pro Val Glu Lys Asn Leu Val Glu Val Asp Gly Lys Lys Tyr Ala
                85                  90                  95

Val Tyr Val Gly Asn Arg Val Ser Leu Ala His Gln Val Gln Val His
            100                 105                 110

Gly Pro Ala Val Ile Arg Asp Asp Thr Phe Val Gly Met Lys Ser Leu
            115                 120                 125

Val Phe Lys Ser Tyr Val Gly Ser Asn Cys Val Ile Glu Pro Gly Val
        130                 135                 140

Leu Leu Met Gly Val Thr Val Ala Asp Gly Arg Tyr Val Pro Ala Gly
145                 150                 155                 160

Ser Val Val Lys Thr Gln Glu Gln Ala Asp Ala Leu Pro Val Ile Thr
                165                 170                 175

Asp Asp Tyr Pro Met Lys Glu Met Asn Lys Gly Val Leu His Val Asn
            180                 185                 190

Lys Ala Leu Ala Arg Gly Tyr Leu Ala Ala Gly Ser
            195                 200

<210> SEQ ID NO 5
<211> LENGTH: 248
<212> TYPE: PRT
<213> ORGANISM: Methanosarcina barkeri

<400> SEQUENCE: 5

Met Arg Phe Asn Lys Gln Thr Phe Thr Ile Leu Ile Leu Ser Leu Ser
1               5                   10                  15
```

```
Leu Ala Leu Leu Gly Ser Gly Cys Ile Ser Glu Gly Glu Gly Ala Glu
            20                  25                  30

Gly Asn Val Thr Gln Gly Ile Thr Glu Ser Glu Phe Ser Asn Ile Arg
            35                  40                  45

Glu Asn Pro Val Thr Pro Trp Asn Pro Val Pro Val Ala Pro Val Ile
50                      55                  60

Asp Pro Thr Ala Phe Ile Asp Pro Gln Ala Ser Val Ile Gly Asn Val
65                  70                  75                  80

Thr Ile Gly Ala Ser Val Met Val Ser Pro Met Ala Ser Ile Arg Ser
                85                  90                  95

Asp Glu Gly Met Pro Ile Phe Val Gly Asp Arg Ser Asn Val Gln Asp
                100                 105                 110

Gly Val Val Leu His Ala Leu Glu Thr Ile Asp Glu Glu Gly Glu Pro
            115                 120                 125

Val Glu Asn Asn Ile Val Glu Val Gly Gly Lys Lys Tyr Ala Val Tyr
            130                 135                 140

Ile Gly Glu Asn Val Ser Leu Ala His Gln Ala Gln Val His Gly Pro
145                 150                 155                 160

Ala Ser Val Gly Asn Asp Thr Phe Ile Gly Met Gln Ala Phe Val Phe
                165                 170                 175

Lys Ser Lys Ile Gly Asn Asn Cys Val Leu Glu Pro Thr Ser Ala Ala
                180                 185                 190

Ile Gly Val Thr Val Pro Asp Gly Arg Tyr Ile Pro Ala Gly Met Val
            195                 200                 205

Val Thr Ser Gln Ala Glu Ala Asp Asn Leu Ser Glu Ile Thr Asp Asp
    210                 215                 220

Tyr Ala Tyr Lys His Thr Asn Glu Ala Val Val Tyr Val Asn Val His
225                 230                 235                 240

Leu Ala Glu Gly Tyr Asn Lys Ala
                245

<210> SEQ ID NO 6
<211> LENGTH: 247
<212> TYPE: PRT
<213> ORGANISM: Methanosarcina acetivorans

<400> SEQUENCE: 6

Met Lys Ile Asn Arg Ile Phe Leu Ala Leu Leu Phe Ser Leu Ala Leu
1               5                   10                  15

Thr Leu Ala Gly Ser Gly Cys Val Ser Gln Gly Glu Gly Ala Glu Asp
            20                  25                  30

Gly Glu Ser Ala Asp Thr Glu Val Glu Ser Glu Val Ser Asn Ile Arg
            35                  40                  45

Ala Asn Pro Val Thr Pro Trp Asn Pro Glu Pro Thr Glu Pro Val Ile
            50                  55                  60

Asp Ser Thr Ala Tyr Ile His Pro Gln Ala Ala Val Ile Gly Asp Val
65                  70                  75                  80

Thr Ile Gly Ala Ser Val Met Val Ser Pro Met Ala Ser Val Arg Ser
                85                  90                  95

Asp Glu Gly Thr Pro Ile Phe Val Gly Asp Glu Thr Asn Ile Gln Asp
                100                 105                 110

Gly Val Val Leu His Ala Leu Glu Thr Val Asn Glu Glu Gly Glu Pro
            115                 120                 125

Val Glu Ser Asn Leu Val Glu Val Asp Gly Glu Lys Tyr Ala Val Tyr
            130                 135                 140
```

Val Gly Glu Arg Val Ser Leu Ala His Gln Ser Gln Ile His Gly Pro
145                 150                 155                 160

Ala Tyr Val Gly Asn Asp Thr Phe Ile Gly Met Gln Ala Leu Val Phe
                165                 170                 175

Lys Ala Asn Val Gly Asp Asn Cys Val Leu Glu Pro Lys Ser Gly Ala
            180                 185                 190

Ile Gly Val Thr Ile Pro Asp Gly Arg Tyr Ile Pro Ala Gly Thr Val
        195                 200                 205

Val Thr Ser Gln Ala Glu Ala Asp Glu Leu Pro Glu Val Thr Asp Asp
    210                 215                 220

Tyr Gly Tyr Lys His Thr Asn Glu Ala Val Val Tyr Val Asn Val Asn
225                 230                 235                 240

Leu Ala Ala Gly Tyr Asn Ala
                245

<210> SEQ ID NO 7
<211> LENGTH: 243
<212> TYPE: PRT
<213> ORGANISM: Methanosarcina mazei

<400> SEQUENCE: 7

Met Ala Leu Leu Leu Ser Leu Ala Ile Thr Leu Ala Gly Ser Gly Cys
1               5                   10                  15

Val Ser Gln Gly Glu Gly Ala Glu Gly Glu Asn Ile Glu Ala Glu
            20                  25                  30

Glu Val Glu Ala Asn Val Glu Glu Ser Asn Ile Arg Ala Asn Pro Val
            35                  40                  45

Thr Pro Trp Asn Pro Glu Pro Thr Glu Pro Val Ile Asp Pro Thr Ala
        50                  55                  60

Tyr Ile His Pro Gln Ala Ser Val Ile Gly Asp Val Thr Ile Gly Ala
65                  70                  75                  80

Ser Val Met Val Ser Pro Met Ala Ser Val Arg Ser Asp Glu Gly Met
                85                  90                  95

Pro Ile Phe Val Gly Asp Glu Cys Asn Ile Gln Asp Gly Val Ile Leu
            100                 105                 110

His Ala Leu Glu Thr Val Asn Glu Glu Gly Glu Pro Val Glu Glu Asn
        115                 120                 125

Gln Val Glu Val Asp Gly Lys Lys Tyr Ala Val Tyr Ile Gly Glu Arg
    130                 135                 140

Val Ser Leu Ala His Gln Ala Gln Val His Gly Pro Ser Leu Val Gly
145                 150                 155                 160

Asn Asp Thr Phe Ile Gly Met Gln Thr Phe Val Phe Lys Ala Lys Ile
                165                 170                 175

Gly Asn Asn Cys Val Leu Glu Pro Thr Ser Ala Ala Ile Gly Val Thr
            180                 185                 190

Val Pro Asp Gly Arg Tyr Ile Pro Ala Gly Thr Val Val Thr Ser Gln
        195                 200                 205

Asp Glu Ala Asp Lys Leu Pro Glu Val Thr Asp Tyr Ala Tyr Lys
    210                 215                 220

His Thr Asn Glu Ala Val Val Tyr Val Asn Thr Asn Leu Ala Glu Gly
225                 230                 235                 240

Tyr Asn Ala

<210> SEQ ID NO 8

```
<211> LENGTH: 275
<212> TYPE: PRT
<213> ORGANISM: Bacillus halodurans

<400> SEQUENCE: 8

Met Lys Lys Tyr Leu Trp Gly Lys Thr Cys Leu Val Val Ser Leu Ser
1               5                   10                  15

Val Met Val Thr Ala Cys Ser Ser Ala Pro Ser Thr Glu Pro Val Asp
                20                  25                  30

Glu Pro Ser Glu Thr His Glu Thr Ser Gly Gly Ala His Glu Val
            35                  40                  45

His Trp Ser Tyr Thr Gly Asp Thr Gly Pro Glu His Trp Ala Glu Leu
        50                  55                  60

Asp Ser Glu Tyr Gly Ala Cys Ala Gln Gly Glu Gln Ser Pro Ile
65                  70                  75                  80

Asn Leu Asp Lys Ala Glu Ala Val Asp Thr Asp Thr Glu Ile Gln Val
                85                  90                  95

His Tyr Glu Pro Ser Ala Phe Thr Ile Lys Asn Asn Gly His Thr Ile
            100                 105                 110

Gln Ala Glu Thr Thr Ser Asp Gly Asn Thr Ile Glu Ile Asp Gly Lys
        115                 120                 125

Glu Tyr Thr Leu Val Gln Phe His Phe His Ile Pro Ser Glu His Glu
130                 135                 140

Met Glu Gly Lys Asn Leu Asp Met Glu Leu His Phe Val His Lys Asn
145                 150                 155                 160

Glu Asn Asp Glu Leu Ala Val Leu Gly Val Leu Met Lys Ala Gly Glu
                165                 170                 175

Glu Asn Glu Glu Leu Ala Lys Leu Trp Ser Lys Leu Pro Ala Glu Glu
            180                 185                 190

Thr Glu Glu Asn Ile Ser Leu Asp Glu Ser Ile Asp Leu Asn Ala Leu
        195                 200                 205

Leu Pro Glu Ser Lys Glu Gly Phe His Tyr Asn Gly Ser Leu Thr Thr
210                 215                 220

Pro Pro Cys Ser Glu Gly Val Lys Trp Thr Val Leu Ser Glu Pro Ile
225                 230                 235                 240

Thr Val Ser Gln Glu Gln Ile Asp Ala Phe Ala Glu Ile Phe Pro Asp
                245                 250                 255

Asn His Arg Pro Val Gln Pro Trp Asn Asp Arg Asp Val Tyr Asp Val
            260                 265                 270

Ile Thr Glu
        275

<210> SEQ ID NO 9
<211> LENGTH: 263
<212> TYPE: PRT
<213> ORGANISM: Bacillus clausii

<400> SEQUENCE: 9

Met Lys Arg Ser His Leu Phe Thr Ser Ile Thr Leu Ala Ser Val Val
1               5                   10                  15

Thr Leu Ala Thr Ala Pro Ala Ala Ser Ala Ala Ser Phe Leu Ser Pro
                20                  25                  30

Leu Gln Ala Leu Lys Ala Ser Trp Ser Tyr Glu Gly Glu Thr Gly Pro
            35                  40                  45

Glu Phe Trp Gly Asp Leu Asp Glu Ala Phe Ala Ala Cys Ser Asn Gly
        50                  55                  60
```

```
Lys Glu Gln Ser Pro Ile Asn Leu Phe Tyr Asp Arg Glu Gln Thr Ser
 65                  70                  75                  80

Lys Trp Asn Trp Ala Phe Ser Tyr Ser Glu Ala Ala Phe Ser Val Glu
                 85                  90                  95

Asn Asn Gly His Thr Ile Gln Ala Asn Val Glu Asn Glu Asp Ala Gly
            100                 105                 110

Gly Leu Glu Ile Asn Gly Glu Ala Tyr Gln Leu Ile Gln Phe His Phe
            115                 120                 125

His Thr Pro Ser Glu His Thr Ile Glu Glu Thr Ser Phe Pro Met Glu
        130                 135                 140

Leu His Leu Val His Ala Asn His Ala Gly Asp Leu Ala Val Leu Gly
145                 150                 155                 160

Val Leu Met Glu Met Gly Asn Asp His Glu Gly Ile Glu Ala Val Trp
                165                 170                 175

Glu Val Met Pro Glu Glu Gly Thr Ala Ala Tyr Ser Ile Ser Leu
            180                 185                 190

Asp Pro Asn Leu Phe Leu Pro Glu Ser Val Thr Ala Tyr Gln Tyr Asp
            195                 200                 205

Gly Ser Leu Thr Thr Pro Pro Cys Ser Glu Gly Val Lys Trp Thr Val
210                 215                 220

Leu Asn Asp Thr Ile Ser Ile Ser Glu Thr Gln Leu Asp Ala Phe Arg
225                 230                 235                 240

Asp Ile Tyr Pro Gln Asn Tyr Arg Pro Val Gln Glu Leu Gly Asp Arg
                245                 250                 255

Glu Ile Gly Phe His Tyr His
            260

<210> SEQ ID NO 10
<211> LENGTH: 240
<212> TYPE: PRT
<213> ORGANISM: Bacillus clausii

<400> SEQUENCE: 10

Ala Ser Ala Ala Ser Phe Leu Ser Pro Leu Gln Ala Leu Lys Ala Ser
 1               5                  10                  15

Trp Ser Tyr Glu Gly Asp Thr Gly Pro Glu Phe Trp Gly Asp Leu Asp
                 20                  25                  30

Glu Ala Phe Ala Ala Cys Ser Asn Gly Lys Glu Gln Ser Pro Ile Asn
             35                  40                  45

Leu Phe Tyr Asp Arg Glu Gln Thr Pro Lys Trp Asn Trp Ala Phe Ser
 50                  55                  60

Tyr Ser Glu Ala Ala Phe Ser Val Glu Asn Asn Gly His Thr Ile Gln
 65                  70                  75                  80

Ala Asn Val Glu Asn Glu Asp Ala Gly Gly Leu Glu Ile Asn Gly Glu
                 85                  90                  95

Ala Tyr Gln Leu Thr Gln Phe His Phe His Thr Pro Ser Glu His Thr
            100                 105                 110

Ile Glu Glu Thr Ser Phe Pro Met Glu Leu His Leu Val His Ala Asn
            115                 120                 125

His Ala Gly Asp Leu Ala Val Leu Gly Val Leu Met Glu Ile Gly Asn
        130                 135                 140

Asp His Glu Gly Ile Glu Ala Val Trp Glu Val Met Pro Glu Glu Glu
145                 150                 155                 160

Gly Thr Ala Glu Tyr Ser Ile Ser Ile Asp Pro Ser Leu Phe Leu Pro
```

165                 170                 175
Glu Ser Val Thr Ala Tyr Gln Tyr Asp Gly Ser Leu Thr Thr Pro Pro
            180                 185                 190

Cys Ser Glu Gly Val Lys Trp Thr Val Leu Asn Asp Thr Ile Ser Ile
        195                 200                 205

Ser Ala Thr Gln Leu Asp Ala Phe Arg Ala Ile Tyr Pro Gln Asn Tyr
    210                 215                 220

Arg Pro Val Gln Glu Leu Gly Asp Arg Glu Ile Gly Phe His Tyr His
225                 230                 235                 240

<210> SEQ ID NO 11
<211> LENGTH: 234
<212> TYPE: PRT
<213> ORGANISM: Bacillus plakortidis

<400> SEQUENCE: 11

Met Ser Lys Met Lys Thr Leu Arg Lys Leu Ser Leu Tyr Ala Ala Phe
1               5                   10                  15

Thr Leu Ser Ser Ser Ser Met Val Thr Ala Pro Leu Phe Ala Gln Thr
            20                  25                  30

Asp Thr His Gln Pro Leu Ile Pro Tyr His Ser Leu His Leu Leu Leu
        35                  40                  45

His Ser Asn Glu Lys Glu Gly Trp Ser Tyr Ser Gly Ser Thr Gly Pro
    50                  55                  60

Gln Phe Trp Ala Asp Leu His Asp Glu Tyr Ile Ala Cys Ser Gln Gly
65                  70                  75                  80

Lys Glu Gln Ser Pro Val Ala Leu His Asn Glu Asp Ala Ser Asp Glu
                85                  90                  95

Gly Lys Trp Ser Leu Asp Leu Asp Tyr Asn Glu Thr Asp Phe Ser Ile
            100                 105                 110

Glu Asn Asn Gly His Thr Ile Gln Ala Asn Val Gly Asp His Ser Ser
        115                 120                 125

Asn Lys Leu Ile Val Asn Gly Thr Asp Tyr Lys Leu Ala Gln Phe His
    130                 135                 140

Phe His Ser Gln Ser Glu His Thr Leu Asp Asp Tyr Tyr Glu Met
145                 150                 155                 160

Glu Leu His Leu Val His Gln Asp Glu Glu Asp Asn Leu Ala Val Leu
                165                 170                 175

Gly Val Leu Ile Glu Glu Gly Glu Lys Asn Glu Thr Leu Ala Asn Met
            180                 185                 190

Trp Asp Val Ile Pro Glu Thr Glu Gly Glu Ala Asp Glu Thr Ile Ser
        195                 200                 205

Leu Asn Pro Ser Glu Leu Val Pro Lys Asp Pro Leu Val Ser Thr Cys
    210                 215                 220

Arg Arg Ala Ser Ser Ser Phe Cys Ser Leu
225                 230

<210> SEQ ID NO 12
<211> LENGTH: 276
<212> TYPE: PRT
<213> ORGANISM: Bacillus plakortidis

<400> SEQUENCE: 12

Met Arg Lys Thr Asn Val Leu Leu Lys Ser Thr Met Ile Thr Thr Leu
1               5                   10                  15

Leu Leu Ser Ser Thr Leu Leu Val Thr Thr Pro Ile Tyr Ala His Thr

-continued

```
                   20                  25                  30
Glu Thr Gln Gln Leu Ser Tyr Lys Thr Leu Asn Asp Leu Leu Thr Glu
                35                  40                  45

Asp Gly His Ser Gly Trp Ser Tyr Ser Gly Leu Thr Gly Pro Glu Tyr
        50                  55                  60

Trp Gly Glu Leu Asn Glu Asp Tyr Lys Ala Cys Ser Lys Gly Glu Glu
65                  70                  75                  80

Gln Ser Pro Ile Ala Leu Gln Asn Glu Asp Ile Asp Asn Glu Lys Trp
                85                  90                  95

Ser Phe Asp Leu Asp Tyr Glu Glu Thr Glu Phe Ser Ile Glu Asn Asn
                100                 105                 110

Gly His Thr Ile Gln Ala Asn Val Glu Gly Ser Ser Ser Asn Thr Leu
            115                 120                 125

Leu Leu Asn Asp Thr Glu Tyr Asn Leu Val Gln Phe His Phe His Ser
            130                 135                 140

Pro Ser Glu His Thr Leu Asp Asp Glu Tyr Phe Glu Met Glu Val His
145                 150                 155                 160

Leu Val His Gln Asp Glu His Ala Asn Leu Ala Val Leu Gly Val Leu
                165                 170                 175

Ile Glu Glu Gly Glu Gln Asn Glu Thr Leu Thr Asp Met Trp Glu Leu
                180                 185                 190

Met Pro Gly Gln Gln Gly Glu Ala Ala Glu Arg Ile Thr Leu Asn Pro
            195                 200                 205

Ser Glu Leu Val Pro Ser Asp Leu Ser Thr Phe Gln Tyr Asp Gly Ser
        210                 215                 220

Leu Thr Thr Pro Pro Cys Ser Glu Asp Val Lys Trp Ser Val Ser Asp
225                 230                 235                 240

Ser Thr Ile Ser Leu Ser Pro Glu Gln Leu Glu Ala Phe Gln Asp Leu
                245                 250                 255

Tyr Pro Asn Asn Tyr Arg Pro Ile Gln Asp Leu Gly Asn Arg Glu Val
            260                 265                 270

Gly Phe His Tyr
            275
```

USE OF ENZYMES HAVING SILICASE ACTIVITY

CROSS-REFERENCE TO RELATED APPLICATIONS

This application is a 35 U.S.C. 371 national application of PCT/EP2009/067551 filed Dec. 18, 2009, which claims priority or the benefit under 35 U.S.C. 119 of European application no. 08172374.4 filed on Dec. 19, 2008 and U.S. provisional application no. 61/139,066 filed on Dec. 19, 2008, the contents of which are fully incorporated herein by reference.

REFERENCE TO A SEQUENCE LISTING

This application contains a Sequence Listing which is hereby incorporated by reference.

FIELD OF THE INVENTION

The present invention relates to the use of polypeptides having silicase activity for the modification or synthesis of silica, silicones and other silicium (IV) compounds and the technical use thereof.

BACKGROUND OF THE INVENTION

After oxygen, silicon is the most abundant element in the earth's crust, and it is essential for growth and biological function in a variety of plant, animal, and microbial systems (Schröder, H. C.; Krasko, A.; Le Pennec, G.; Adell, T.; Wiens, M.; Hassanein, H.; Müller, I. M.; Müller, W. E. G., Progress in Molecular and Subcellular Biology, 2003, 33, 249-268). Silicon is found in the form of free silicates ($SiO4^{x-}$, the salts of silicic acid) and bound silica (a hydrated polymer of $SiO_2$). Silica occurs commonly in nature as sandstone, silica sand or quartzite, wherein it is a hydrated polymer that exist in three different crystalline forms: quartz, tridymite and cristobalite. Of these, only quartz is common. Liquid silica does not readily crystallize but instead solidifies to a glass (Douglas, B. E.; Ho, S.-M. Crystal structures of silica and metal silicates. In Structure and Chemistry of Crystalline Solids, Springer: New York, 2006, 233). Silica is the starting material for the manufacture of ceramics and silicate glasses. In addition it is used as filler in a large variety of applications such as paints, plastics, rubber, adhesives, putty and sealants. In addition, a range of precious stones such as amethyst, agate, jasper, and opal are a build up of silica.

The silicates are by far the largest and the most complicated class of minerals. Approximately 30% of all minerals are silicates and some geologists estimate that 90% of the Earth's crust is made up of silicates. Examples of silicate minerals are feldspar, asbestos, clay, hornblende, and zeolites. On top of this the neosilicates (also known as orthosilicates) present a range of precious stones such as olivine, topaz, and zircon (Douglas, B. E.; Ho, S.-M. Crystal structures of silica and metal silicates. In Structure and Chemistry of Crystalline Solids, Springer: New York, 2006, 233).

Biosilicification occurs globally on a vast scale under mild conditions (e.g. neutral pH and low temperature). In fact, minute planktonic algae (diatoms) control the marine silica cycle and these single-cell plants process gigatons of particulate silica every year (Brandstadt, K. F. Curr. Opin. Biotechnol. 2005, 16, 393 and references herein). In addition to diatoms, also sponges, mollusks and higher plants can carry out biosilicification (Shimizu, K.; Cha, J. N.; Stucky, G. D.; Morse, D. E., Proc. Natl. Acad. Sci. USA, 1998, 95, 6234 and references herein).

The synthesis of silica (biosilicification) is catalyzed by the so called silicateins (Shimizu et al. Proc. Natl. Acad. Sci. USA, 1998, 95, 6234., Zhou, Y.; Shimizu, K.; Cha, J. N.; Stucky, G. D.; Morse, D. E., Angew. Chem. Int. Ed., 1999, 38, 780. Alber, B.; Ferry, J., Proc. Natl. Acad. Sci. USA, 1994, 91, 6909) and as is usually the case in nature, enzymes with the reverse activity (silicase activity i.e. hydrolysis of silica to silicic acid) has been reported from marine sponges (e.g. Suberites domuncula), were the released silicic acid is used by other organisms for making silica skeletons (Cha, J. N.; Shimizu, K.; Zhou, Y.; Christiansen, S. C.; Chmelka, B. F.; Stucky, G. D.; Morse, D. E., Proc. Natl. Acad. Sci. USA, 1999, 96, 361).

Silicase activity has also been reported to be present as an additional activity of an alpha-carbonic anhydrase (Cha et al Proc. Natl. Acad. Sci. USA, 1999, 96, 361), Schroder et al., Progress in Molecular and Subcellular Biology, 2003, 33,249-268, and Muller et all, US Patent Publication No. 2007/0218044.

SUMMARY OF THE INVENTION

The present invention relates to the use of polypeptides having silicase activity for the modification or synthesis of silica, silicones and other silicium (IV) compounds. The present invention also relates to the use of polypeptides having silicase activity for the modification of glass, sand, asbestos, computer chips, glass wool, fiber glass, optical fibers (e.g., fictionalization of the fibers), silicones, for the separation of sand from oil-sands (e.g., by increased dissolution of the sand), for the removal of asbestos, and for sandblasting.

One aspect of the present invention relates to a method for the modification of silica, silicone and a silicium (IV) compounds, comprising treating silica, silicone or a silicium compound with a gamma-carbonic anhydrase having silicase activity.

Yet another aspect of the present invention relates to a method for the synthesis of silica, silicone and a silicium (IV) compounds, comprising treating a precursor of silica, silicone or a silicium compound with a gamma-carbonic anhydrase having silicase activity, wherein the treatment results in the synthesis of silica, silicone and a silicium (IV) compounds.

The present invention also relates to a method for the modification of silica, silicone and a silicium (IV) compounds, comprising treating silica, silicone or a silicium compound with a silicase obtained from *Methanosarcina thermophila* or a silicase activity which has a high degree of amino acid sequence identity to the *Methanosarcina thermophila* silicase (SEQ ID NO: 1).

The present invention also provides a method for the synthesis of silica, silicone and a silicium (IV) compounds, comprising treating a precursor of silica, silicone or a silicium compound with a silicase obtained from *Methanosarcina thermophila* or a silicase activity which has a degree of amino acid sequence identity to the *Methanosarcina thermophila* silicase (SEQ ID NO: 1), wherein the treatment results in the synthesis of silica, silicone and a silicium (IV) compounds.

Another aspect of the present invention relates to a method for the modification of silica, silicone and a silicium (IV) compounds, comprising treating silica, silicone or a silicium compound with a silicase obtained from *Bacillus plakortidis, Bacillus clausii* or *Bacillus haludurons* or an enzyme having silicase activity which has a high degree of amino acid sequence identity to the *Bacillus plakortidis* silicase (SEQ ID NO:11 or 12), *Bacillus clausii* silicase (SEQ ID NO:9 or 10) or *Bacillus haludurons* (SEQ ID NO:8).

Yet another aspect of the present invention provides a method for the synthesis of silica, silicone and a silicium (IV) compounds, comprising treating a precursor of silica, silicone or a silicium compound with a silicase obtained from *Bacillus plakortidis, Bacillus clausii* or *Bacillus haludurons* or an enzyme having silicase activity which has a high degree of amino acid sequence identity to the *Bacillus plakortidis* silicase (SEQ ID NO:11 or 12), *Bacillus clausii* silicase (SEQ ID NO:9 or 10) or *Bacillus haludurons* (SEQ ID NO:8), wherein the treatment results in the synthesis of silica, silicone and a silicium (IV) compounds.

DETAILED DESCRIPTION OF THE INVENTION

As used herein, a "silicase" or a polypeptide "having silicase activity" is an enzyme that catalyzes the inter conversion between silica and silicic acid. Silicases can hydrolyze amorphous and crystalline silicon dioxide to form free silicic acid, and due to the reversibility of the reaction, silicases can also synthesize silicone dioxide (as condensation products of silicic acid, silicates), silicones and other silicium (IV) compounds. Silicase activity may be determined according to the procedure described in Example III.

In some embodiments, polypeptides having silicase activity include polypeptides having "carbonic anhydrase" activity as well. Carbonic anhydrases (also termed "carbonate dehydratases") catalyze the inter-conversion between carbon dioxide and bicarbonate. Carbonic anhydrases are generally classified under the enzyme classification (EC 4.2.1.1). Carbonic anhydrase activity may be determined according to the procedures described in Example II Carbonic anhydrases are widely distributed in nature in all domains of life (Smith, K. and Ferry, J. J. Bacteriol., 1999, 181, 6247; Smith, K. and Ferry, J. FEMS Microbiol. Rev., 2000, 24, 335). These enzymes have three distinct classes: the alpha-class, the beta-class and the gamma-class (Hewett-Emmett, D. and Tashian, R. Mol. Phylogenet. Evol., 1996, 5, 50). A fourth class (the delta class) has been proposed recently (So et al., J. Bacteriol., 2004, 186, 623). These classes evolved from independent origins (Bacteria, Archaea, Eukarya) with distinct protein sequence compositions, structures and functionalities. Alpha-carbonic anhydrases are abundant in all mammalian tissues where they facilitate the removal of $CO_2$. In prokaryotes, genes encoding all three carbonic anhydrase classes have been identified, with the beta- and gamma-class predominating.

The inventors have discovered the presence of silicase activity in the gamma-carbonic anhydrase enzyme family, and this enzyme family may be used for the modification or synthesis of silica, silicones and other silicium (IV) compounds Examples of gamma-carbonic anhydrases having silicase activity include the gamma-carbonic anhydrase obtained from *Methanosarcina thermophila* strain TM-1 (Alber and Ferry, 1994, Proc. Natl. Acad. Sci. USA 91: 6909-6913; Alber and Ferry, 1996, J. Bacteriol. 178: 3270-3274). The amino acid sequence of the gamma-carbonic anhydrase from *Methanosarcina thermophila* is shown as SEQ ID NO:1, and is also described in WO 2008/095057. The X-ray structure of gamma-carbonic anhydrase from *Methanosarcina thermophila* has also been reported (Strop et al., J. Biol. Chem, 2001, 276, 10299).

As used herein, the term "obtained" means that the enzyme may have been isolated from an organism which naturally produces the enzyme as a native enzyme. The "obtained" enzymes may, however, be reproduced recombinantly in a host organism.

Gamma-carbonic anhydrases having silicase activity may be identified and obtained from other sources including microorganisms isolated from nature (e.g., soil, composts, water, etc.). Examples of other sources of known gamma-carbonic anhydrase include the carbonic anhydrases from *Pelobacter carbinolicus* (SEQ ID NO:2), *Syntrophus acidtrophicus* (SEQ ID NO:4), *Bacillus licheniformis* (SEQ ID NO:5), *Methanosarcina acetivorans* (SEQ ID NO:6), *Methanosarcina barkeri* (SEQ ID NO:5), *Methanosarcina mazei* (SEQ ID NO:7). The presence of silicase activity can be confirmed by the procedure described in Example III.

Gamma-carbonic anhydrases having silicase activity may also be identified and obtained from other sources including microorganisms isolated from nature (e.g., soil, composts, water, etc.) by using nucleic acid probes, e.g., as described in WO 2008/095057. Techniques for isolating microorganisms from natural habitats are well known in the art. The polynucleotide may then be obtained by similarly screening a genomic or cDNA library of another microorganism or by genome sequencing. Once a polynucleotide sequence encoding a polypeptide has been detected with the probe(s), the polynucleotide can be isolated or cloned by utilizing techniques which are well known to those of ordinary skill in the art. The presence of silicase activity can be confirmed by the procedure described in Example III.

Other silicases for use in the present invention include polypeptides having silicase activity which have a degree of identity to the *Methanosarcina thermophila* silicase (SEQ ID NO: 1) of at least 60%, more preferably at least 65%, more preferably at least 70%, more preferably at least 75%, more preferably at least 80%, more preferably at least 85%, even more preferably at least 90%, most preferably at least 95%, and even most preferably at least 96%, at least 97%, at least 98%, or at least 99%.

As used herein, the degree of "identity" between two amino acid sequences is determined using the Needleman-Wunsch algorithm (Needleman and Wunsch, 1970, J. Mol. Biol. 48: 443-453) as implemented in the Needle program of the EMBOSS package (EMBOSS: The European Molecular Biology Open Software Suite, Rice et al., 2000, Trends in Genetics 16: 276-277), preferably version 3.0.0 or later. The parameters used are gap open penalty of 10, gap extension penalty of 0.5, and the EBLOSUM62 (EMBOSS version of BLOSUM62) substitution matrix (or corresponding parameters in another program used to determine % identity). The output of Needle labeled "longest identity" (obtained using the—nobrief option) is used as the percent identity and is calculated as follows: (Identical Residues×100)/(Length of Alignment−Total Number of Gaps in Alignment).

Suitable silicase enzymes for use in the present invention include polypeptides that are substantially homologous to the *Methanosarcina thermophila* silicase (SEQ ID NO:1). "Substantially homologous polypeptides" may have one or more amino acid substitutions, deletions or additions. These changes are preferably of a minor nature, that is conservative amino acid substitutions and other substitutions that do not significantly affect the three-dimensional folding or activity of the protein or polypeptide; small deletions, typically of one to about 30 amino acids; amino- or carboxyl-terminal extensions, such as an amino-terminal methionine residue, a small linker peptide of up to about 20-25 residues, or a small extension that facilitates purification (an affinity tag), such as a poly-histidine tract, or protein A (Nilsson et al., 1985, EMBO J. 4: 1075; Nilsson et al., 1991, Methods Enzymol. 198: 3. See, also, in general, Ford et al., 1991, Protein Expression and Purification 2: 95-107.

Suitable silicase enzymes for use in the present invention also include polypeptides that have silicase activity and differ from *Methanosarcina thermophila* silicase (SEQ ID NO:1) by up to thirty amino acids, by up to twenty-nine amino acids, by up to twenty-eight amino acids, by up to twenty-seven amino acids, by up to twenty-six amino acids, by up to twenty-five amino acids, by up to twenty-four amino acids, by up to twenty-three amino acids, by up to twenty-two amino acids, by up to twenty-one amino acids, by up to twenty- amino acids, by up to nineteen amino acids, by up to eighteen amino acids, by up to seventeen amino acids, by up to sixteen amino acids, by up to fifteen amino acids, by up to fourteen amino acids, by up to thirteen amino acids, by up to twelve amino acids, by up to eleven amino acids, by up to ten amino acids, by up to nine amino acids, by up to eight amino acid, by up to seven amino acids, by up to six amino acids, by up to five amino acids, by up to four amino acids, by up to three amino acids, by up to two amino acids, or by one amino acid.

Examples of conservative substitutions are within the group of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions that do not generally alter specific activity are known in the art and are described, for example, by H. Neurath and R. L. Hill, 1979, In, The Proteins, Academic Press, New York. The most commonly occurring exchanges are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly. A limited number of non-conservative amino acids, amino acids that are not encoded by the genetic code, and unnatural amino acids may be substituted for amino acid residues, such as, pipecolic acid, thiazolidine carboxylic acid, dehydroproline, 3- and 4-methylproline, and 3,3-dimethylproline.

Essential amino acids in the *Methanosarcina thermophila* silicase (SEQ ID NO:1) silicase can also be identified according to procedures known in the art, such as site-directed mutagenesis or alanine-scanning mutagenesis (Cunningham and Wells, 1989, Science 244: 1081-1085). In the latter technique, single alanine mutations are introduced at every residue in the molecule, and the resultant mutant molecules are tested for biological activity (i.e., silicase activity) to identify amino acid residues that are critical to the activity of the molecule. See also, Hilton et al., 1996, J. Biol. Chem. 271: 4699-4708. The active site of the enzyme or other biological interaction can also be determined by physical analysis of the structure, as determined by such techniques as nuclear magnetic resonance, crystallography, electron diffraction, or photoaffinity labeling, in conjunction with mutation of putative contact site amino acids. See, for example, de Vos et al., 1992, Science 255: 306-312; Smith et al., 1992, J. Mol. Biol. 224: 899-904; Wlodaver et al., 1992, FEBS Lett. 309: 59-64. The identities of essential amino acids can also be inferred from analysis of identities with polypeptides that are related to a polypeptide according to the invention.

Single or multiple amino acid substitutions, deletions, and/or insertions can be made and tested using known methods of mutagenesis, recombination, and/or shuffling, followed by a relevant screening procedure, such as those disclosed by Reidhaar-Olson and Sauer, 1988, Science 241: 53-57; Bowie and Sauer, 1989, Proc. Natl. Acad. Sci. USA 86: 2152-2156; WO 95/17413; or WO 95/22625. Other methods that can be used include error-prone PCR, phage display (e.g., Lowman et al., 1991, Biochem. 30: 10832-10837; U.S. Pat. No. 5,223, 409; WO 92/06204), and region-directed mutagenesis (Derbyshire et al., 1986, Gene 46: 145; Ner et al., 1988, DNA 7: 127).

Mutagenesis/shuffling methods can be combined with high-throughput, automated screening methods to detect activity of cloned, mutagenized polypeptides expressed by host cells (Ness et al., 1999, Nature Biotechnology 17: 893-896). Mutagenized DNA molecules that encode active polypeptides can be recovered from the host cells and rapidly sequenced using standard methods in the art. These methods allow the rapid determination of the importance of individual amino acid residues in a polypeptide of interest, and can be applied to polypeptides of unknown structure.

Silicases for use in the present invention also include fragments of the *Methanosarcina thermophila* silicase (SEQ ID NO:1) having silicase activity. A fragment of the *Methanosarcina thermophila* silicase (SEQ ID NO:1) is a polypeptide having one or more amino acids deleted from the amino and/or carboxyl terminus of this amino acid sequence. For example, the fragment may comprise SEQ ID NO:1 having a truncation at the C terminus of up to 20 amino acid residues, more preferably up to 10 amino acid residues, and most preferably up to 5 amino acid residues.

In addition to the above silicase enzymes, the present invention is further directed to the use of certain alpha-carbonic anhydrases which have also been determined to have silicase activity, in particular, the silicases from *Bacillus plakortidis* (formerly *Bacillus gibsonii*) shown as SEQ ID NO:11 or 12 which possess both silicase activity and carbonic anhydrase activity, and the silicase from *Bacillus clausii* (SEQ ID NO:10) which also posses both silicase activity and carbonic anhydrase activity. Suitable silicases also includes polypeptides having silicase activity and having a degree of identity to the *Bacillus plakortidis* silicase (SEQ ID NO: 10 or 11) or *Bacillus clausii* silicase (SEQ ID NO:9 or 10) of preferably at least 60%, more preferably at least 65%, more preferably at least 70%, more preferably at least 75%, more preferably at least 80%, more preferably at least 85%, even more preferably at least 90%, most preferably at least 95%, and even most preferably at least 96%, at least 97%, at least 98%, or at least 99%. The cloning and expression of the *B. clausii* carbonic anhydrase is described in WO 2008/09057. The preparation of the carbonic anhydrase from *B. plakortidis* is described in WO 2007/019859.

The present invention is also directed to the use the silicase from *Bacillus haludurons* shown as SEQ ID NO: 8. Suitable silicases also includes polypeptides having silicase activity and having a degree of identity to the *Bacillus haludurons* (SEQ ID NO: 8) of preferably at least 0%, more preferably at least 65%, more preferably at least 70%, more preferably at least 75%, more preferably at least 80%, more preferably at least 85%, even more preferably at least 90%, most preferably at least 95%, and even most preferably at least 96%, at least 97%, at least 98%, or at least 99%. The cloning and expression of the *B. haludurons* carbonic anhydrase is described in WO 2008/095057.

Suitable silicases for use in the present invention also include polypeptides having silicase activity and that differ from the silicase obtained from *Bacillus plakortidis* silicase (SEQ ID NO:11 or 12), *Bacillus clausii* silicase (SEQ ID NO:9 or 10) or *Bacillus haludurons* (SEQ ID NO:8) by up to thirty amino acids, by up to twenty-nine amino acids, by up to twenty-eight amino acids, by up to twenty-seven amino acids, by up to twenty-six amino acids, by up to twenty-five amino acids, by up to twenty-four amino acids, by up to twenty-three amino acids, by up to twenty-two amino acids, by up to twenty-one amino acids, by up to twenty-amino acids, by up to nineteen amino acids, by up to eighteen amino acids, by up to seventeen amino acids, by up to sixteen amino acids, by up to fifteen amino acids, by up to fourteen amino acids, by up to thirteen amino acids, by up to twelve amino acids, by up to eleven amino acids, by up to ten amino acids, by up to nine amino acids, by up to eight amino acid, by up to seven amino acids, by up to six amino acids, by up to five amino acids, by up to four amino acids, by up to three amino acids, by up to two amino acids, or by one amino acid.

Silicases for use in the present invention also include fragments of the *Bacillus plakortidis* silicase (SEQ ID NO:11 or 12), *Bacillus clausii* silicase (SEQ ID NO:9 or 10) or *Bacillus haludurons* silicase (SEQ ID NO:8) having silicase activity. A fragment of the *Bacillus plakortidis* silicase (SEQ ID NO:11 or 12), *Bacillus clausii* silicase (SEQ ID NO:9 or 10) *Bacillus haludurons* silicase (SEQ ID NO:8) is a polypeptide having one or more amino acids deleted from the amino and/or carboxyl terminus of this amino acid sequence. For example, a fragment can include SEQ ID NO:8, 9, 10 or 11 truncated at the N-terminus by up to 20 amino acids, up to 10 amino acids, up to 5 amino acids.

The silicases disclosed herein for use in the present invention may be an isolated polypeptide. The term "isolated polypeptide" as used herein refers to a polypeptide that is isolated from a source. In a preferred aspect, the polypeptide is at least 1% pure, preferably at least 5% pure, more preferably at least 10% pure, more preferably at least 20% pure, more preferably at least 40% pure, more preferably at least 60% pure, even more preferably at least 80% pure, and most preferably at least 90% pure, as determined by SDS-PAGE.

The silicases disclosed herein for use in the present invention may be substantially pure. The term "substantially pure polypeptide" denotes herein a polypeptide preparation that contains at most 10%, preferably at most 8%, more preferably at most 6%, more preferably at most 5%, more preferably at most 4%, more preferably at most 3%, even more preferably at most 2%, most preferably at most 1%, and even most preferably at most 0.5% by weight of other polypeptide material with which it is natively or recombinantly associated. It is, therefore, preferred that the substantially pure polypeptide is at least 92% pure, preferably at least 94% pure, more preferably at least 95% pure, more preferably at least 96% pure, more preferably at least 96% pure, more preferably at least 97% pure, more preferably at least 98% pure, even more preferably at least 99%, most preferably at least 99.5% pure, and even most preferably 100% pure by weight of the total polypeptide material present in the preparation. The polypeptides of the present invention are preferably in a substantially pure form, i.e., that the polypeptide preparation is essentially free of other polypeptide material with which it is natively or recombinantly associated. This can be accomplished, for example, by preparing the polypeptide by well-known recombinant methods or by classical purification methods.

In accordance with the present invention, the silicases disclosed herein are used in a method for the modification of silica, silicones or silicium (IV) compounds as well as of mixed polymers of these compounds using the silicase enzymes described herein. As used herein, "modification" includes the hydrolysis or degradation of silica, silicones and other silicium (IV) compounds.

In another embodiment of this aspect of the invention, the present invention provides a method for synthesizing silica, silicones or silicium (IV) compounds as well as of mixed polymers of these compounds using the silicase enzymes described herein. In an embodiment, the method comprises a method for the synthesis of silica, silicone and a silicium (IV) compounds, comprising treating a precursor of silica, silicone or a silicium compound with a silicase enzyme described herein, wherein the treatment results in the synthesis of silica, silicone and a silicium (IV) compounds.

The enzymes having silicase activity may be used in the modification or synthesis of a compound selected from the group consisting of such as silicic acids, monoalkoxy silantrioles, dialkoxy silandioles, trialkoxy silanoles, tetraalkoxy silanes, alkyl- or aryl-silantrioles, alkyl- or aryl-monoalkoxy silandioles, alkyl- or aryl-dialkoxy silanoles, alkyl- or aryl-trialkoxy silanes or other metal(IV)-compounds.

Technical uses of the polypeptides having silicase activity include in the modification of glass, sand, asbestos, computer chips, glass wool, fiber glass, optical fibers, and silicones. For example, modification of silica can be used for changing the surface of glass, e.g., to provide dirt repellent window glass, to adhere solar cells to window glass, to adhere sun shading materials to window glass, etc.

The polypeptides may also be used to modify the properties of fillers, such as, Sipernat and Aerosil, where other chemical groups could be attached to the polymeric silica. This functionality could also be used for the modification of silicones, where more delicate functionalization could be perform via the enzymatic reaction compared to the standard chemical reaction.

The polypeptides may also be used to separate sand from oil-sands, to get rid of waste asbestos, or to provide sandblasting under extremely mild conditions.

The silicases are used in amount effective to modify or synthesize silica, silicones or silicium (IV) compounds. The amount effective will vary depending on the technical application, and such amount can be determined by one of ordinary skill in the art. Appropriate temperature, pH and other reaction conditions can also be determined by one of ordinary skill in the art.

Silicases for use in the methods of the present invention may be formulated in any suitable form for the intended technical applications, such as, as a liquid, e.g., aqueous form, a as granulates, non-dusting granulates, or as a dry powder or as a protected enzymes.

EXAMPLES

Example I

The carbonic anhydrase gene from *Methanosarcina thermophila* (UNIPROT: P40881) was synthetically produced and codon optimized for *Bacillus subtilis*. The gene sequence coding for the native signal peptide was exchanged to the alpha-amylase from *B. licheniformis* (AmyL) by SOE fusion as described in WO 99/43835 (hereby incorporated by reference) in frame to the DNA encoding the carbonic anhydrase. The nucleotide fragments obtained from containing the carbonic anhydrase coding sequence were integrated by homologous recombination into the *Bacillus subtilis* host cell genome. The gene construct was expressed under the control of a triple promoter system (as described in WO 99/43835). The gene coding for chloramphenicol acetyltransferase was used as maker, as described in (Diderichsen et al., 1993, Plasmid 30: 312-315).

Chloramphenicol resistant transformants were analyzed by DNA sequencing to verify the correct DNA sequence of the construct. One expression clone for each recombinant sequence was selected.

The individual carbonic anhydrase expression clones were fermented on a rotary shaking table in 1 L baffled Erlenmeyer flasks each containing 400 ml soy based media supplemented with 34 mg/l chloramphenicol. The clones were fermented for 4 days at 37° C.

The recombinant carbonic anhydrase were purified to homogeneity: The culture broth was centrifuged (26.000×g, 20 min) and the supernatant was filtered through a Whatman 0.45 μm filter. The 0.45 μm filtrate was approx. pH 7 and conductivity was approx. 20 mS/cm. The 0.45 μm filtrate was transferred to 10 mM HEPES/NaOH, pH 7.0 by G25 sephadex chromatography and then applied to a Q-sepharose FF column. Bound protein was eluted with a linear NaCl gradient. Fractions were collected during elution and these fractions were tested for carbonic anhydrase activity.

Example II

Detection of Carbonic Anhydrase Activity

The carbonic anhydrase activity in the culture broth and of the purified protein was determined according to (Wilbur, 1948, J Biol Chem 176: 147-154). Alternatively, the carbonic anhydrase activity was measured as esterase activity with para-nitrophenolacetate as substrate according to (Chirica et al., 2001, Biochim Biophys Acta 2001 Jan. 12; 1544 (1-2): 55-63 1544: 55-63). Details can be found in the patent application WO2008/095057 which is hereby incorporated as reference.

Example III

Silica Hydrolysis
Buffer

A buffer cocktail containing 50 mM glycine, 50 mM citric acid, 50 mM sodium phosphate, 50 mM dithiothreitol, 100 mM NaCl, and 0.5 mM $ZnSO_4$ was applied, with the pH values adjusted to 2.5, 5.0, 7.5, and 10.0 with HCl or NaOH. Buffers were made with silicate free water (Merck 1.16754.9010) in plastic containers.

Substrates

The following silica substrates were used; as a representative for crystalline silica sand (white quartz, Sigma-Aldrich 274739) was chosen, and for amorphous silica, Sipernat® 22S and Aerosil® 200 (both Degussa, now Evonik) were chosen. Sipernat and Aerosil are produced by two different methods; precipitation and pyrolysis respectively, which could give rise to differing surface properties and hence sensitivity towards enzymatic action.

TABLE 1

Properties of the silica forms

| Silica | Solid form | Surface area ($m^2/g$) | Average particle size (μm) |
|---|---|---|---|
| Sand | Crystals | — | 210-297 |
| Sipernat ® 22S | Amorphous | 190.0 | 7 |
| Aerosil ® 200 | Amorphous | 200 ± 25 | 0.012 |

Hydrolytic Activity

In 1.5 mL Eppendorf tubes 5 mg substrate and enzyme solution corresponding to 100 μg enzyme was suspended in 1.0 mL buffer. Blind determinations were run with 5 mg substrate in 1.0 mL buffer. The mixtures were incubated with shaking at room temperature (or 50° C.) overnight. After 20-23 hours the suspensions were centrifuged (13.400 rpm, 15 min, 4° C.), and 700 μL of the supernatant was filtered. For this, Durapore Millex-GV 22 μm 13 mm diameter filters were used.

300 μL of the filtrate was added to 4.7 mL buffer and to determine the amount of free silicic acid, the Merck Silicate Assay (1.14794) was conducted. This colorimetric assay is based on the reaction between silicate and molybdate ions to form a yellow heteropoly acid. This acid is then reduced to silicomolybdenum blue, which can be detected spectrophotometrically at 810 nm.

The absolute amounts of silicic acid were calculated after construction of a calibration curve using a silicium standard (Merck 170236). Linearity was observed from 0 to 2.5 μg silicic acid/mL. Everything was conducted in plastic containers to avoid silicate dissolution from glass.

Example IV

Hydrolysis of Aerosil® 200 by Methanosarcina thermophila Carbonic Anhydrase

Applying the experimental conditions described in Example III with Aerosil as substrate and M. thermophila carbonic anhydrase as enzyme gives the results shown in Table 2.

TABLE 2

Silicate formation (g/l*h*g enzyme)

| Silicate formation (g/l*h*g enzyme) | pH 2.5 | pH 5.0 | pH 7.5 | pH 10 |
|---|---|---|---|---|
| Control | 0.24 ± 0.03 | 0.26 ± 0.05 | 0.47 ± 0.10 | 2.71 ± 0.77 |
| Methanosarcina thermophila carbonic anhydrase | 0.62 ± 0.05 | 0.85 ± 0.10 | 0.99 ± 0.08 | 5.63 ± 3.19 |
| Net silicate formation | 0.38 | 0.59 | 0.52 | 2.92 |

Example V

Hydrolysis of Aerosil® 200 by B. clausii Carbonic Anhydrase

Applying the experimental conditions described in Example IV with Aerosil as substrate and B. clausii carbonic anhydrase as enzyme gives the results shown in Table 3.

TABLE 3

Silicate formation (g/l*h*g enzyme)

| Silicate formation (g/l*h*g enzyme) | pH 2.5 | pH 5.0 | pH 7.5 | pH 10 |
|---|---|---|---|---|
| Control | 0.24 ± 0.03 | 0.26 ± 0.05 | 0.47 ± 0.10 | 2.71 ± 0.77 |
| Bacillus clausii carbonic anhydrase | 0.30 ± 0.02 | 0.78 ± 0.06 | 0.89 ± 0.07 | 4.36 ± 1.00 |
| Net silicate formation | 0.06 | 0.52 | 0.42 | 1.65 |

Example VI

Hydrolysis of Aerosil® 200 by B. plakortidis Carbonic Anhydrase

Applying the experimental conditions described in Example IV with Aerosil as substrate and B. plakortidis carbonic anhydrase as enzyme gives the results shown in Table 4.

TABLE 4

| Silicate formation (g/l * h * g enzyme) | | | | |
|---|---|---|---|---|
| Silicate formation (g/l * h * g enzyme) | pH 2.5 | pH 5.0 | pH 7.5 | pH 10 |
| Control | 0.24 ± 0.03 | 0.26 ± 0.05 | 0.47 ± 0.10 | 2.71 ± 0.77 |
| Bacillus plakortidis carbonic anhydrase | 0.18 ± 0.01 | 0.33 ± 0.04 | 0.96 ± 0.05 | 4.59 ± 1.74 |
| Net silicate formation | 0.06 | 0.07 | 0.50 | 1.88 |

Example VII

Hydrolysis of Sipernat® 22S by *Methanosarcina thermophila* Carbonic Anhydrase

Applying the experimental conditions described in Example IV with Sipernat® 22S as substrate and *M. thermophila* carbonic anhydrase as enzyme gives the results shown in Table 5.

TABLE 5

| Silicate formation (g/l * h * g enzyme) | | | | |
|---|---|---|---|---|
| Silicate formation (g/l * h * g enzyme) | pH 2.5 | pH 5.0 | pH 7.5 | pH 10 |
| Control | 0.45 ± 0.13 | 1.25 ± 0.62 | 0.79 ± 0.51 | 3.68 ± 1.60 |
| Methanosarcina thermophila carbonic anhydrase | 0.43 ± 0.07 | 0.86 ± 0.09 | 2.71 ± 0.52 | 8.43 ± 0.83 |
| Net silicate formation | −0.02 | −0.39 | 1.92 | 4.75 |

Example VIII

Hydrolysis of Sipernat® 22S by *B. clausii* Carbonic Anhydrase

Applying the experimental conditions described in Example IV with Sipernat® 22S as substrate and *B. clausii* carbonic anhydrase as enzyme gives the results shown in Table 6.

TABLE 6

| Silicate formation (g/l * h * g enzyme) | | | | |
|---|---|---|---|---|
| Silicate formation (g/l * h * g enzyme) | pH 2.5 | pH 5.0 | pH 7.5 | pH 10 |
| Control | 0.45 ± 0.13 | 1.25 ± 0.62 | 0.79 ± 0.51 | 3.68 ± 1.60 |
| Bacillus clausii carbonic anhydrase | 0.95 ± 0.05 | 0.50 ± 0.30 | 0.65 ± 0.12 | 1.45 ± 0.41 |
| Net silicate formation | 0.50 | — | — | — |

Example IX

Hydrolysis of Sipernat® 22S by *B. plakortidis* Carbonic Anhydrase

Applying the experimental conditions described in Example IV with Sipernat® 22S as substrate and *B. plakortidis* carbonic anhydrase as enzyme gives the results shown in Table 7.

TABLE 7

| Silicate formation (g/l * h * g enzyme) | | | | |
|---|---|---|---|---|
| Silicate formation (g/l * h * g enzyme) | pH 2.5 | pH 5.0 | pH 7.5 | pH 10 |
| Control | 0.45 ± 0.13 | 1.25 ± 0.62 | 0.79 ± 0.51 | 3.68 ± 1.60 |
| Bacillus plakortidis carbonic anhydrase | 0.32 ± 0.01 | 0.48 ± 0.05 | 1.47 ± 0.27 | 7.49 ± 3.79 |
| Net silicate formation | — | — | 0.68 | 3.81 |

Example X

Hydrolysis of Sand by *Methanosarcina thermophila* Carbonic Anhydrase

Applying the experimental conditions described in Example IV with sand as substrate and *M. thermophila* carbonic anhydrase as enzyme gives the results shown in Table 8.

TABLE 8

| Silicate formation (g/l * h * g enzyme) | | | | |
|---|---|---|---|---|
| Silicate formation (g/l * h * g enzyme) | pH 2.5 | pH 5.0 | pH 7.5 | pH 10 |
| Control | 0.10 ± 0.01 | 0.05 ± 0.00 | 0.15 ± 0.02 | 0.64 ± 0.11 |
| Methanosarcina thermophila carbonic anhydrase | 0.16 ± 0.003 | 0.23 ± 0.01 | 0.34 ± 0.01 | 0.68 ± 0.08 |
| Net silicate formation | 0.06 | 0.18 | 0.19 | — |

Example XI

Hydrolysis of Sand by *B. clausii* Carbonic Anhydrase

Applying the experimental conditions described in Example IV with sand as substrate and *Bacillus clausii* carbonic anhydrase as enzyme gives the results shown in Table 9.

TABLE 9

| Silicate formation (g/l * h * g enzyme) | | | | |
|---|---|---|---|---|
| Silicate formation (g/l * h * g enzyme) | pH 2.5 | pH 5.0 | pH 7.5 | pH 10 |
| Control | 0.10 ± 0.01 | 0.05 ± 0.00 | 0.15 ± 0.02 | 0.64 ± 0.11 |
| Bacillus clausii carbonic anhydrase | 0.03 ± 0.00 | 0.15 ± 0.01 | 0.27 ± 0.03 | 0.69 ± 0.01 |
| Net silicate formation | — | 0.10 | 0.12 | 0.05 |

Example XII

Hydrolysis of Sand by *B. plakortidis* Carbonic Anhydrase

Applying the experimental conditions described in Example IV with sand as substrate and *Bacillus plakortidis* carbonic anhydrase as enzyme gives the results shown in Table 10.

TABLE 10

| Silicate formation (g/l * h * g enzyme) | | | | |
|---|---|---|---|---|
| Silicate formation (g/l * h * g enzyme) | pH 2.5 | pH 5.0 | pH 7.5 | pH 10 |
| Control | 0.10 ± 0.01 | 0.05 ± 0.00 | 0.15 ± 0.02 | 0.64 ± 0.11 |
| *Bacillus plakortidis* carbonic anhydrase | 0.35 ± 0.06 | 0.05 ± 0.00 | 0.15 ± 0.01 | 0.64 ± 0.01 |
| Net silicate formation | 0.26 | 0.00 | 0.01 | 0.00 |

Example XIII

Hydrolysis of Glass Wool by *B. clausii* Carbonic Anhydrase

Applying the experimental conditions described in Example III with Glass wool (Supelco, Sigma Aldrich 20384 (non-treated)) as substrate and *Bacillus clausii* carbonic anhydrase as enzyme gives the results shown in Table 11.

For the experiments at pH 10, a buffer without phosphate was used: 50 mM glycine, 50 mM dithiothreitol, 100 mM NaCl, and 0.5 mM $ZnSO_4$. pH was adjusted with HCl.

TABLE 11

| Silicate formation (g/l * h * g enzyme) | | | | |
|---|---|---|---|---|
| Silicate formation (g/l * h * g enzyme) | pH 2.8 | pH 5.0 | pH 7.5 | pH 10 |
| Control | 0.48 ± 0.02 | 0.55 ± 0.09 | 0.38 ± 0.04 | 4.63 ± 0.28 |
| *Bacillus clausii* carbonic anhydrase | 0.52 ± 0.04 | 0.63 ± 0.03 | 0.63 ± 0.04 | 6.49 ± 0.78 |
| Net silicate formation | 0.04 | 0.08 | 0.25 | 1.86 |

Example XIV

Hydrolysis of Glass Wool by *B. plakortidis* Carbonic Anhydrase

Applying the experimental conditions described in Example III with Glass wool as substrate and *Bacillus plakortidis* carbonic anhydrase as enzyme gives the results shown in Table 12.

TABLE 12

| Silicate formation (g/l * h * g enzyme) | | |
|---|---|---|
| Silicate formation (g/l * h * g enzyme) | pH 2.8 | pH 5.0 |
| Control | 0.48 ± 0.02 | 0.55 ± 0.09 |
| *Bacillus plakortidis* carbonic anhydrase | 3.37 ± 0.74 | 1.05 ± 0.24 |

TABLE 12-continued

| Silicate formation (g/l * h * g enzyme) | | |
|---|---|---|
| Silicate formation (g/l * h * g enzyme) | pH 2.8 | pH 5.0 |
| Net silicate formation | 2.89 | 0.50 |

Example XV

Hydrolysis of Glass Wool by *Methanosarcina thermophila* Carbonic Anhydrase

Applying the experimental conditions described in Example III with Glass wool as substrate and *Methanosarcina thermophila* carbonic anhydrase as enzyme gives the results shown in Table 13.

For the experiments at pH 10, a buffer without phosphate was used: 50 mM glycine, 50 mM dithiothreitol, 100 mM NaCl, and 0.5 mM $ZnSO_4$. pH was adjusted with HCl.

TABLE 13

| Silicate formation (g/l * h * g enzyme) | | | | |
|---|---|---|---|---|
| Silicate formation (g/l *h * g enzyme) | pH 2.8 | pH 5.0 | pH 7.5 | pH 10 |
| Control | 0.48 ± 0.02 | 0.55 ± 0.09 | 0.38 ± 0.04 | 4.63 ± 0.28 |
| *Methanosarcina thermophila* carbonic anhydrase | 0.39 ± 0.02 | 0.36 ± 0.01 | 0.71 ± 0.18 | 3.15 ± 0.12 |
| Net silicate formation | −0.09 | −0.19 | 0.33 | −1.48 |

Example XVI

Hydrolysis of Asbestos by *B. clausii* Carbonic Anhydrase

Applying the experimental conditions described in Example III with Asbestos (25 mg, 20% brown asbestos, Skandinavisk Bio-Medicinsk Institut NS, Denmark) as substrate and *Bacillus clausii* carbonic anhydrase as enzyme gives the results shown in Table 14.

For the experiments at pH 10, a buffer without phosphate was used: 50 mM glycine, 50 mM dithiothreitol, 100 mM NaCl, and 0.5 mM $ZnSO_4$. pH was adjusted with HCl.

TABLE 14

| Silicate formation (g/l * h * g enzyme) | | | | |
|---|---|---|---|---|
| Silicate formation (g/l * h * g enzyme) | pH 2.8 | pH 5.0 | pH 7.5 | pH 10 |
| Control | 0.39 ± 0.03 | 0.75 ± 0.05 | 0.29 ± 0.01 | 0.48 ± 0.03 |
| *Bacillus clausii* carbonic anhydrase | 0.61 ± 0.05 | 1.57 ± 0.54 | 0.48 ± 0.01 | 0.63 ± 0.03 |
| Net silicate formation | 0.22 | 0.82 | 0.19 | 0.16 |

Example XVII

Hydrolysis of Asbestos by *Methanosarcina thermophila* Carbonic Anhydrase

Applying the experimental conditions described in Example III with Asbestos (25 mg, 20% brown asbestos) as substrate and *Methanosarcina thermophila* carbonic anhydrase as enzyme gives the results shown in Table 15.

For the experiments at pH 10, a buffer without phosphate was used: 50 mM glycine, 50 mM dithiothreitol, 100 mM NaCl, and 0.5 mM $ZnSO_4$. pH was adjusted with HCl.

TABLE 15

| Silicate formation (g/l * h * g enzyme) | | | | |
|---|---|---|---|---|
| Silicate formation (g/l * h * g enzyme) | pH 2.8 | pH 5.0 | pH 7.5 | pH 10 |
| Control | 0.39 ± 0.03 | 0.75 ± 0.05 | 0.29 ± 0.01 | 0.48 ± 0.03 |
| *Methanosarcina thermophila* carbonic anhydrase | 0.69 ± 0.02 | 35.98 ± 3.89 | 9.95 ± 3.16 | 1.10 ± 0.18 |
| Net silicate formation | 0.30 | 35.35 | 9.65 | 0.62 |

```
SEQUENCE LISTING
Methanosarcina thermophila
                                            (SEQ ID NO: 1)
MMFNKQIFTILILSLSLALAGSGCISEGAEDNVAQEITVDEFSNIREN

PVTPWNPEPSAPVIDPTAYIDPQASVIGEVTIGANVMVSPMASIRSDE

GMPIFVGDRSNVQDGVVLHALETINEEGEPIEDNIVEVDGKEYAVYIG

NNVSLAHQSQVHGPAAVGDDTFIGMQAFVFKSKVGNNCVLEPRSAAIG

VTIPDGRYIPAGMVVTSQAEADKLPEVTDDYAYSHTNEAVVYVNVHLA

EGYKETS

Bacillus licheniformis
                                            (SEQ ID NO: 2)
MKLSSKLILGLTVSSLAGKFLEKLLIQDNVSPNITASFNQEADIPDID

ASSYIHHFASVIGSVVIGRNVFIGPFSSIRGDVGLKIFISHDCNIQDG

VVLHGLKNYEYNSPVTEHSVFKDRESYSIYIGEKVSLAPQCQIYGPVR

IDKNVFVGMQSLVFDAYIQEDTVIEPGAKIIGVTIPPKRFVSAGRVIS

NQEDANRLPEITDSYPYHDLNSKMTSVNLELAKGYKKEERQWKL

Pelobacter carbinolicus
                                            (SEQ ID NO: 3)
MIEKNVVTDFCSEASEPVIDASTYVHPLAAVIGNVILGKNIMVSPTAV

VRGDEGQPLHVGDDSNIQDGVVIHALETEMNGKPVAKNLYQVDGRSYG

AYVGCRVSLAHQVQIHGPAVVLDDTFVGMKSLVFKSFVGKGCVIEPGS

IVMGVTVADGRYVPAGSVIRTQEDADALPEIGADYPFRAMNPGVVHVN

TALAKGYMVKQGN

Syntrophus aciditrophicus
                                            (SEQ ID NO: 4)
MIGKNVLTDFSARASEPVIGSFTFVHPLAAVIGNVILGDNIMVSPGAS

IRGDEGQPLYVGSDSNVQDGVVIHALETELDGKPVEKNLVEVDGKKYA

VYVGNRVSLAHQVQVHGPAVIRDDTFVGMKSLVFKSYVGSNCVIEPGV

LLMGVTVADGRYVPAGSVVKTQEQADALPVITDDYPMKEMNKGVLHVN

KALARGYLAAGS

Methanosarcina barkeri
                                            (SEQ ID NO: 5)
MRFNKQTFTILILSLSLALLGSGCISEGEGAEGNVTQGITESEFSNIR

ENPVTPWNPVPVAPVIDPTAFIDPQASVIGNVTIGASVMVSPMASIRS

DEGMPIFVGDRSNVQDGVVLHALETIDEEGEPVENNIVEVGGKKYAVY

IGENVSLAHQAQVHGPASVGNDTFIGMQAFVFKSKIGNNCVLEPTSAA

IGVTVPDGRYIPAGMVVTSQAEADNLSEITDDYAYKHTNEAVVYVNVH

LAEGYNKA

Methanosarcina acetivorans
                                            (SEQ ID NO: 6)
MKINRIFLALLFSLALTLAGSGCVSQGEGAEDGESADTEVESEVSNIR

ANPVTPWNPEPTEPVIDSTAYIHPQAAVIGDVTIGASVMVSPMASVRS

DEGTPIFVGDETNIQDGVVLHALETVNEEGEPVESNLVEVDGEKYAVY

VGERVSLAHQSQIHGPAYVGNDTFIGMQALVFKANVGDNCVLEPKSGA

IGVTIPDGRYIPAGTVVTSQAEADELPEVTDDYGYKHTNEAVVYVNVN

LAAGYNA

Methanosarcina mazei
                                            (SEQ ID NO: 7)
MALLLSLAITLAGSGCVSQGEGAEEGENIEAEEVEANVEESNIRANPV

TPWNPEPTEPVIDPTAYIHPQASVIGDVTIGASVMVSPMASVRSDEGM

PIFVGDECNIQDGVILHALETVNEEGEPVEENQVEVDGKKYAVYIGER

VSLAHQAQVHGPSLVGNDTFIGMQTFVFKAKIGNNCVLEPTSAAIGVT

VPDGRYIPAGTVVTSQDEADKLPEVTDDYAYKHTNEAVVYVNTNLAEG

YNA

Bacillus halodurans
                                            (SEQ ID NO: 8)
MKKYLWGKTCLVVSLSVMVTACSSAPSTEPVDEPSETHEETSGGAHEV

HWSYTGDTGPEHWAELDSEYGACAQGEEQSPINLDKAEAVDTDTEIQV

HYEPSAFTIKNNGHTIQAETTSDGNTIEIDGKEYTLVQFHFHIPSEHE

MEGKNLDMELHFVHKNENDELAVLGVLMKAGEENEELAKLWSKLPAEE

TEENISLDESIDLNALLPESKEGFHYNGSLTTPPCSEGVKWTVLSEPI

TVSQEQIDAFAEIFPDNHRPVQPWNDRDVYDVITE

Bacillus clausii
                                            (SEQ ID NO: 9)
MKRSHLFTSITLASVVTLATAPAASAASFLSPLQALKASWSYEGETGP

EFWGDLDEAFAACSNGKEQSPINLFYDREQTSKWNWAFSYSEAAFSVE

NNGHTIQANVENEDAGGLEINGEAYQLIQFHFHTPSEHTIEETSFPME

LHLVHANHAGDLAVLGVLMEMGNDHEGIEAVWEVMPEEEGTAAYSISL

DPNLFLPESVTAYQYDGSLTTPPCSEGVKWTVLNDTISISETQLDAFR

DIYPQNYRPVQELGDREIGFHYH

Bacillus clausii
                                            (SEQ ID NO: 10)
ASAASFLSPLQALKASWSYEGDTGPEFWGDLDEAFAACSNGKEQSPIN

LFYDREQTPKWNWAFSYSEAAFSVENNGHTIQANVENEDAGGLEINGE
```

-continued

```
AYQLTQFHFHTPSEHTIEETSFPMELHLVHANHAGDLAVLGVLMEIGN

DHEGIEAVWEVMPEEEGTAEYSISIDPSLFLPESVTAYQYDGSLTTPP

CSEGVKWTVLNDTISISATQLDAFRAIYPQNYRPVQELGDREIGFHYH
```

*Bacillus gibsonii*

(SEQ ID NO: 11)

```
MSKMKTLRKLSLYAAFTLSSSSMVTAPLFAQTDTHQPLIPYHSLHLLL

HSNEKEGWSYSGSTGPQFWADLHDEYIACSQGKEQSPVALHNEDASDE

GKWSLDLDYNETDFSIENNGHTIQANVGDHSSNKLIVNGTDYKLAQFH

FHSQSEHTLDDDYYEMELHLVHQDEEDNLAVLGVLIEEGEKNETLANM

WDVIPETEGEADETISLNPSELVPKDPLVSTCRRASSSFCSL
```

*Bacillus gibsonii*

(SEQ ID NO: 12)

```
MRKTNVLLKSTMITTLLLSSTLLVTTPIYAHTETQQLSYKTLNDLLTE

DGHSGWSYSGLTGPEYWGELNEDYKACSKGEEQSPIALQNEDIDNEKW

SFDLDYEETEFSIENNGHTIQANVEGSSSNTLLLNDTEYNLVQFHFHS

PSEHTLDDEYFEMEVHLVHQDEHANLAVLGVLIEEGEQNETLTDMWEL

MPGQQGEAAERITLNPSELVPSDLSTFQYDGSLTTPPCSEDVKWSVSD

STISLSPEQLEAFQDLYPNNYRPIQDLGNREVGFHY
```

The invention claimed is:

1. A method for the modification of silica, silicone and a silicium (IV) compound, comprising treating silica, silicone or a silicium compound with a gamma-carbonic anhydrase having silicase activity which has at least 90% sequence identity to SEQ ID NO: 1.

2. The method of claim 1, wherein the silicase is obtained from *Methanosarcina thermophila*.

3. A method for the synthesis of silica, silicone and a silicium (IV) compound, comprising treating a precursor of silica, silicone or a silicium compound with a gamma-carbonic anhydrase having silicase activity which has at least 90% sequence identity to SEQ ID NO: 1, wherein the treatment results in the synthesis of silica, silicone and a silicium (IV) compound.

4. The method of claim 3, wherein the silicase is obtained from *Methanosarcina thermophila*.

5. The method of claim 1, wherein the silicase is used for the modification of glass, sand, asbestos, computer chips, glass wool, fiber glass, optical fibers and silicones, for the removal of sand from oil-sands, for the removal of asbestos, or for sandblasting.

6. The method of claim 1, wherein the sequence identity to SEQ ID NO: 1 is at least 95%.

7. The method of claim 1, wherein the sequence identity to SEQ ID NO: 1 is at least 99%.

8. The method of claim 3, wherein the sequence identity to SEQ ID NO: 1 is at least 95%.

9. The method of claim 3, wherein the sequence identity to SEQ ID NO: 1 is at least 99%.

10. The method of claim 1, wherein the sequence identity to SEQ ID NO: 1 is at least 97%.

11. The method of claim 1, wherein the sequence identity to SEQ ID NO: 1 is at least 98%.

12. The method of claim 1, wherein the gamma-carbonic anhydrase having silicase activity is substantially pure.

13. The method of claim 3, wherein the sequence identity to SEQ ID NO: 1 is at least 97%.

14. The method of claim 3, wherein the sequence identity to SEQ ID NO: 1 is at least 98%.

15. The method of claim 3, wherein the gamma-carbonic anhydrase having silicase activity is substantially pure.

* * * * *